United States Patent [19]

Watanabe

[11] 3,992,104

[45] Nov. 16, 1976

[54] AUTOMATIC POLARIZATION ANALYSER DEVICE

[75] Inventor: Sakuji Watanabe, Yono, Japan

[73] Assignee: Nippon Kogaku K.K., Tokyo, Japan

[22] Filed: Aug. 25, 1975

[21] Appl. No.: 607,582

[30] Foreign Application Priority Data

Aug. 29, 1974 Japan............................ 49-98335

[52] U.S. Cl.............................. 356/117; 356/118
[51] Int. Cl.².......................................... G01N 21/40
[58] Field of Search.................... 356/114, 117, 118

[56] References Cited
UNITED STATES PATENTS

| | | |
|---|---|---|
| 3,450,478 | 6/1969 | Sebestyen ........................ 356/117 |
| 3,687,555 | 8/1972 | Yamamoto et al. ............... 356/114 |
| 3,741,661 | 6/1973 | Yamamoto et al. ............... 356/117 |

Primary Examiner—John K. Corbin
Assistant Examiner—Richard A. Rosenberger
Attorney, Agent, or Firm—Shapiro and Shapiro

[57] ABSTRACT

An automatic polarization analyser device which can automatically measure the phase difference and the azimuth angle of a sample and automatically indicate the values of the respective measurements for the phase difference of the sample not only within the range of 0° to 180° but also within the range of 180° to 360°.

13 Claims, 9 Drawing Figures

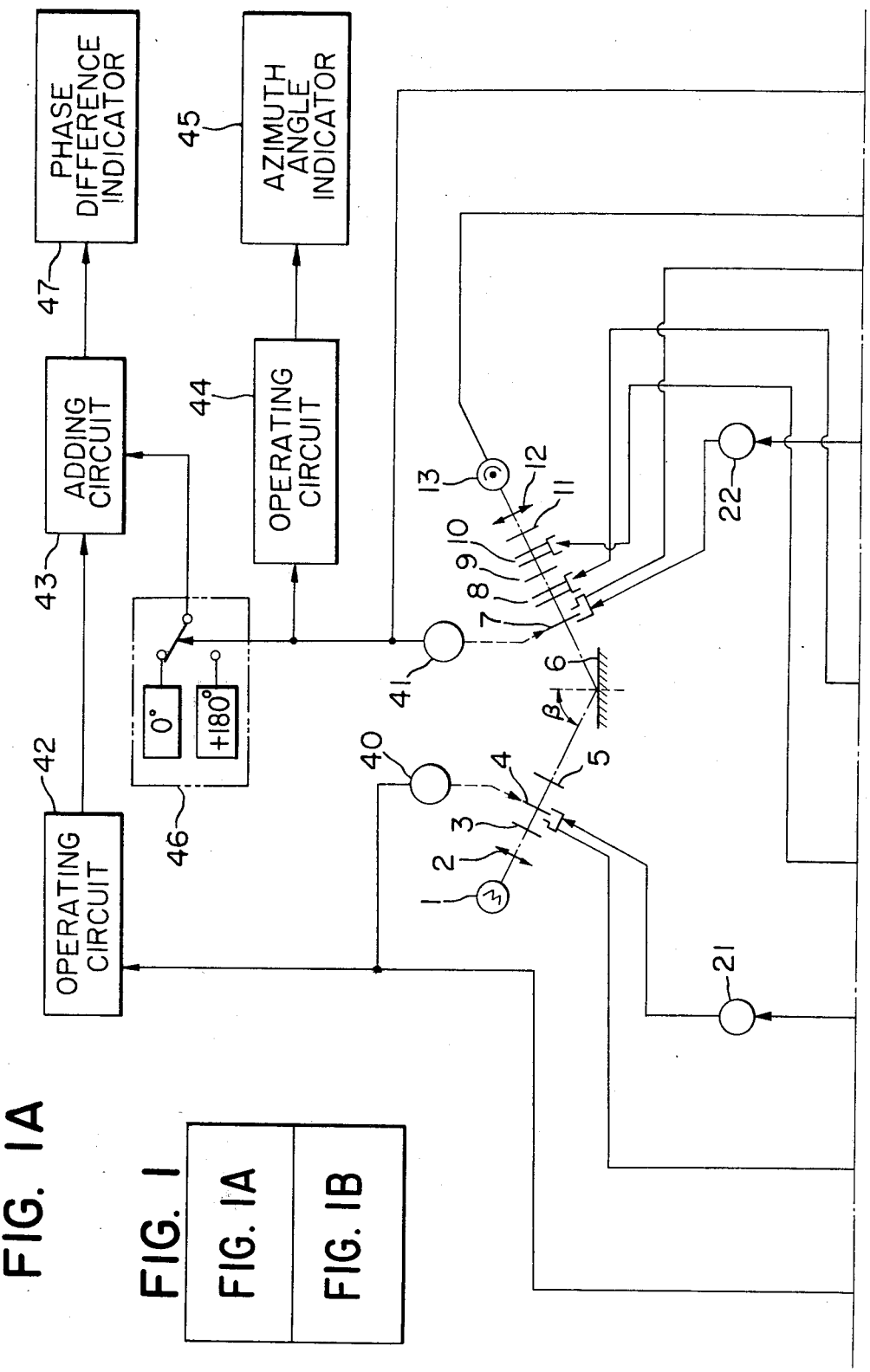

| FIG. 7A | FIG. 7B |

AUTOMATIC POLARIZATION ANALYSER DEVICE

BACKGROUND OF THE INVENTION

1. Field of the Invention

This invention relates to an automatic polarization analyser for measuring a variation in the polarized condition of light when the light has passed through a sample and automatically measuring the phase difference $\Delta$ and the amplitude-reflection ratio angle (azimuth angle) $\Psi$ of the sample to automatically indicate their respective values.

2. Description of the Prior Art

The automatic polarization analyser device to which the present invention relates may be of two types, namely, the reflection type and the transmission type. Where the automatic polarization analyser device is of the reflection type, it has a polarizing optical system comprising a light source, a polarizer mounted for rotation about the optical axis of the system, a ¼ wavelength plate having its azimuth angle set to −45° or +45° with respect to a reference azimuth (the surface of incidence of a sample), a ½ wavelength plate mounted for rotation about the optical axis, light modulator means for phase difference modulation and azimuth angle modulation, an analyser having its azimuth angle set to 0° (if the azimuth angle of the ¼ wavelength plate is −45°) or 90° (if the azimuth angle of the ¼ wavelength plate is +45°) with respect to the reference azimuth, and a photoelectric converter. Where the automatic polarization analyser device is of the transmission type, it has a polarizing optical system comprising a light source, a polarizer mounted for rotation about the optical axis of the system, a ¼ wavelength plate having its azimuth angle set to −45° or +45° with respect to a reference azimuth (the axial azimuth of the analyser), a sample having its axial azimuth set to said reference azimuth, a ½ wavelength plate mounted for rotation about the optical axis, light modulator means for phase difference modulation and azimuth angle modulation, an analyser, and a photoelectric converter. In any of these devices, the polarizer and the ½ wavelength plate are automatically controlled to individually obtain a value which determines the phase difference $\Delta$ of the sample from the angle of rotation of the polarizer and a value which determines the amplitude-reflection ratio angle $\Psi$ of the sample from the angle of rotation of the ½ wavelength plate, whereby the phase difference $\Delta$ and the amplitude-reflection ratio angle $\Psi$ are indicated.

Although these conventional devices can achieve the automatic control and the automatic indication if the phase difference $\Delta$ is within the range of $0° \leq \Delta \leq 180°$, they are disadvantageous in that such automatic control and indication may not be achieved if the phase difference $\Delta$ is within the range of $180° \leq \Delta \leq 360°$.

SUMMARY OF THE INVENTION

The present invention has, for its object, to overcome such a disadvantage and to provide an automatic polarization analyser device which can perform completely automatic control and indication for the phase difference $\Delta$ within the range of $0° \quad \Delta \quad 180°$ as well as within the range of $180° \leq \Delta \leq 360°$.

The invention will be described in detail by reference to the accompanying drawings.

BRIEF DESCRIPTION OF THE DRAWINGS

FIGS. 1, 1A and 1B show a first embodiment of the present invention.

DESCRIPTION OF THE PREFERRED EMBODIMENTS

Figure 1B:
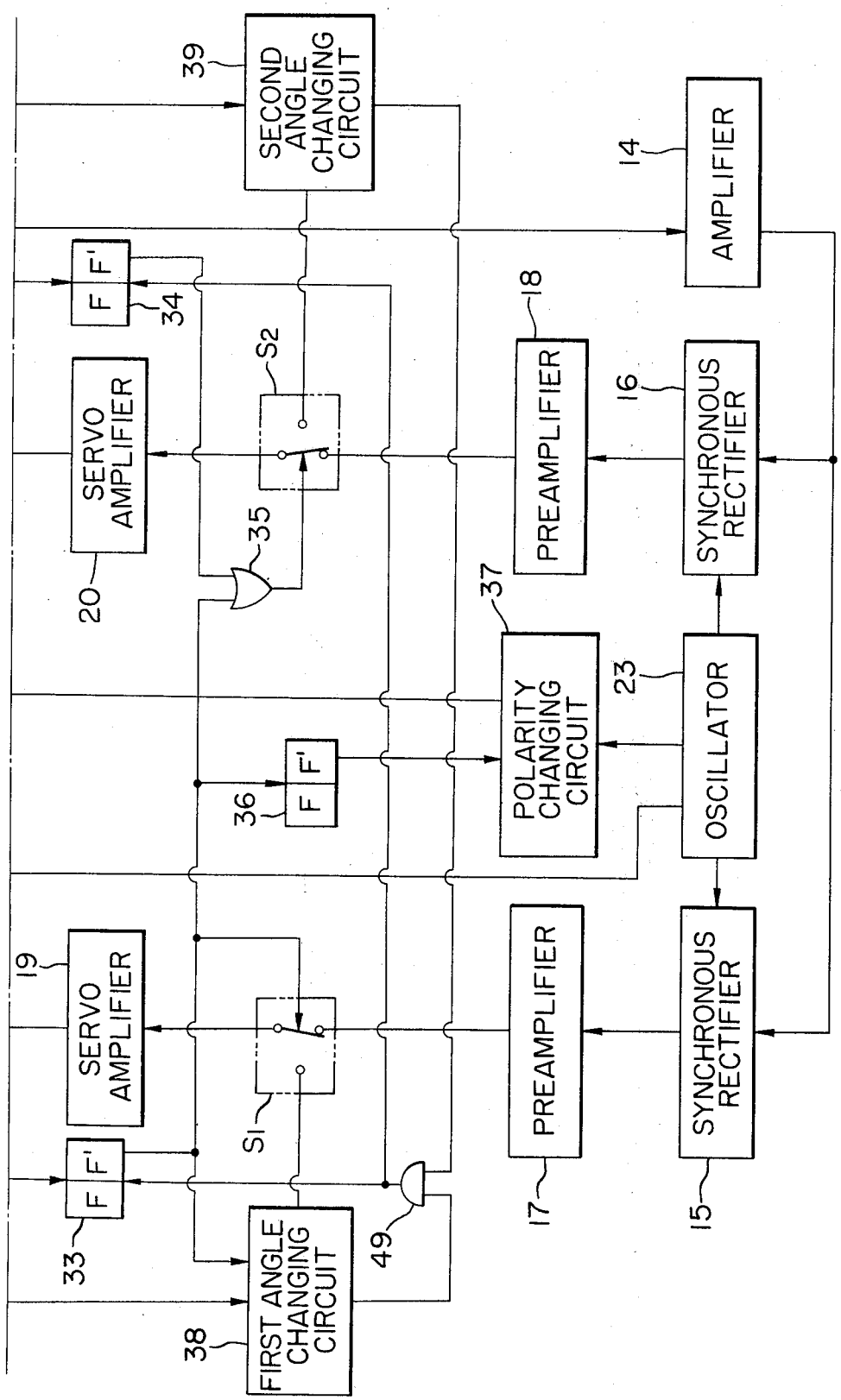
Figure 2:
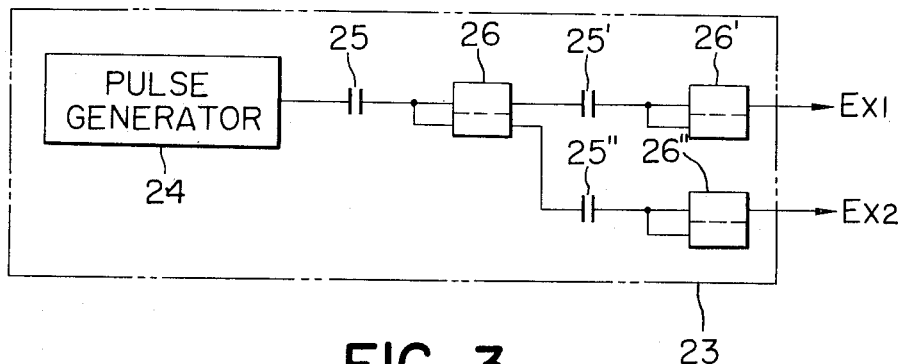
FIG. 2 is a diagram of a specific oscillator circuit employed in the first embodiment.

A first embodiment of the present invention will be described by reference to FIGS. 1 to 6. There is seen a light source 1, a collimator lens 2, an interference filter 3 for deriving a monochromatic light, a polarizer 4 rotatable about the optical axis, a ¼ wavelength plate 5 having its azimuth angle (it being understood that counter-clockwise rotation as viewed from the side of a photoelectric converter 13, which will later be described, is of the positive sense) set to −45° with respect to the reference azimuth (the surface of incidence of a sample 6), the sample 6 being set to a predetermined angle of incidence $\beta$, and a ½ wavelength plate 7 mounted for rotation about the optical axis of the light reflected by the sample 6.

Further provided is a K.D.P. light modulator element 8 having its azimuth angle set to −45° with respect to the reference azimuth, a ¼ wavelength plate 9 having its azimuth angle set to +90° with respect to the reference azimuth, and a K.D.P. light modulator element 10 having its azimuth angle set to −45° with respect to the reference azimuth. These elements 8, 9 and 10 together constitute light modulator means for simultaneously imparting a phase difference modulation and an azimuth angle (amplitude-reflection ratio angle) modulation to linearly polarized light having passed through the ½ wavelength plate 7. There is also provided an analyser 11 having its azimuth angle set to 0° with respect to the reference azimuth, and a telescope 12 for effectively directing the light to a photoelectric converter 13. The elements 1 to 13 together constitute the polarizing optical system in the reflection type of automatic polarization analyser device.

It is assumed that when the light output signal from the analyser 11 has become zero, namely, when the extinguished condition has been attained, the azimuth angle of the polarizer 4 and of the ½ wavelengthh plate 7 with respect to the reference azimuth are $\theta_P$ and $\theta_H$, respectively. Then, the phase difference $\Delta$ and the amplitude-reflection ratio angle $\Psi$ of the sample 6 may be obtained as follows: If $0° \leq \Delta \leq 180°$, the phase difference $\Delta$ will be: $\Delta = 90° + 2\theta_P$, and if $180° \leq \Delta \leq 360°$, $\Delta = 270° + 2\theta_P$.

The amplitude-reflection ratio angle $\Psi$ will be:
$\Psi = |2\theta_H|$.

Description will now be made of a driving circuit 14–41 for automatically controlling the polarizer 4 and the ½ wavelength plate 7 so that the light output signal from the analyser 11 becomes zero, and a circuit 40–47 for calculating and indicating the phase difference $\Delta$ and the amplitude-reflection ratio angle (azimuth angle) $\Psi$.

Designated by 14 is an amplifier for amplifying the photocurrent resulting from the photoelectric conversion by the photoelectric converter 13. Synchronous rectifier circuits 15 and 16 are provided to derive only the signal components in phase with the signal delivered from an oscillator 23, to the described, out of the photocurrent passed through the amplifier 14 and to rectify such signal components.

Denoted by 17 and 18 are preamplifiers, and 19, 20 designate servo amplifiers connected through first and second change-over switch means S1 and S2, respectively. Servo-motors 21 and 22 are provided to rotate the polarizer 4 and the ½ wavelength plate 7, respectively. Designated by 23 is an oscillator for applying an alternating voltage $E_{x1}$ to the synchronous rectifier circuit 15 and the K.D.P. light modulator element 10 and for applying an alternating voltage $E_{x2}$, which is 90° out of phase with $E_{x1}$, to the synchronous rectifier circuit 16 and the K.D.P. light modulator element 8. The oscillator 23 is constituted by elements 24–26 shown in FIG. 2.

Figure 3:
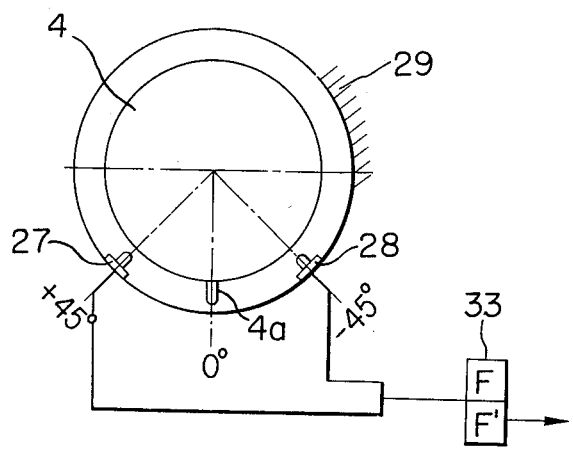
FIG. 3 is a view for illustrating the principle of means for detecting the ±45° rotation of the polarizer.
Figure 4:
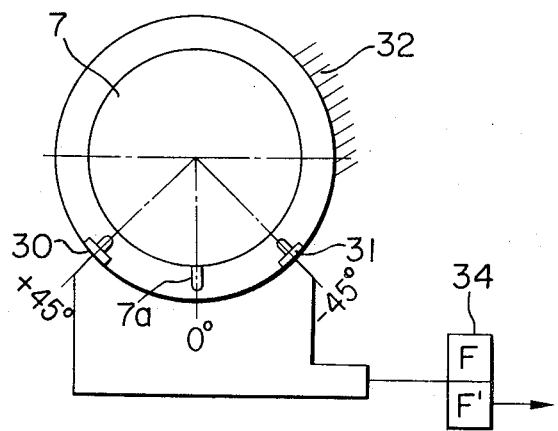
FIG. 4 is a view for illustrating the principle of means for detecting the ±45° rotation of the ½ wavelength plate.

The element 24 is a pulse generator, the elements 25, 25' and 25'' are capacitors, and elements 26, 26' and 26'' are bistable multivibrators. When the bistable multivibrator 26 is driven by the signal passed from the pulse generator 24 through the capacitor 25, two signals 180° out of phase with each other may be provided at the two outputs of the bistable multivibrator 26. Also, when two signals are passed through the capacitors 25' and 25'' to drive the bistable multivibrators 26' and 26'', alternating voltages $E_{x1}$ and $E_{x2}$ 90° out of phase with each other may be provided from these multivibrators 26' and 26''. Referring to FIG. 3, a projection 4a is formed on a peripheral portion of the polarizer 4 which is at the axial azimuth, and microswitches 27 and 28 are provided on a casing 29 at the azimuths of ±45° with respect to the reference azimuth 0° and engageable with the projection 4a. A flip-flop circuit 33 is provided which, upon reception of a signal produced by the microswitch 27 or 28 when engaged with the projection 4a, may be set to ON state and produce an output signal and which may be reset to OFF state upon reception of a high level signal produced by an AND gate 49 which will hereinafter be described. Referring to FIG. 4, a projection 7a, is formed on a peripheral portion of the ½ wavelength plate which is at the axial azimuth, and microswitches 30 and 31 are provided on a casing 32 at the azimuths of ±45° with respect to the reference azimuth 0° and engageable with the projection 7a. A flip-flop circuit 34 is provided which, upon reception of a signal produced by the microswitch 30 or 31 when engaged with the projection 7a, may be set to ON state and produce an output signal and which may be reset to OFF state upon reception of a high level signal produced by an AND circuit 49 which will hereinafter be described. S1 is a first change-over switch which normally connects the preamplifier 17 to the servo amplifier 19 but, upon reception of the output signal from the flip-flop circuit 33 when in its ON state, connects an angle changing circuit 38 to the servo amplifier 19. Designated by 35 is an OR circuit which, upon reception of the output signal from the flip-flop circuit 33 or 34 at one of two inputs of the OR circuit, may produce and deliver an output signal to a second change-over switch S2 which will hereinafter be described. The second change-over switch S2 normally connects the preamplifier 18 to the servo amplifier 20 but, upon reception of the output signal from the OR circuit, connects the angle changing circuit 39 to the servo amplifier 20. A flip-flop circuit 36 is provided which may be set to ON state by the output signal produced from the flip-flop circuit 33 when set to its ON state, and which may be reset to OFF state by the output signal produced from the flip-flop circuit 33 when again set to its ON state after being reset to its OFF state. Designated by 37 is a polarity changing circuit which, upon reception of the output signal from the flip-flop circuit 36 when set to its ON state, may be rendered operative to change the polarity of the alternating voltage $E_{x2}$ applied from the oscillator 23 to the K.D.P. light modulator element 8 and which may return the changed polarityy of the alternating voltage $E_{x2}$ to the original polarity when the flip-flop circuit 36 is reset to its OFF state. A first angle changing circuit 38 is provided which controls the servo-motor 21 so that when the polarizer 4 has been rotated by +45° to bring its projection 4a into engagement with the microswitch 27, and the first changeover switch S1 has been changed over to connect the circuit 38 to the servo amplifier 19, the polarizer 4 may be displaced to its position of −45°, and that when the polarizer 4 has been rotated by −45° to bring its projection 4a into engagement with the microswitch 28 and the first change-over switch S1 has been changed over to connect the circuit 38 to the servo amplifier 19, the polarizer 4 may be displaced to its position of +45°.

The first angle changing circuit will now be discussed with reference to FIG. 5.

Figure 5:
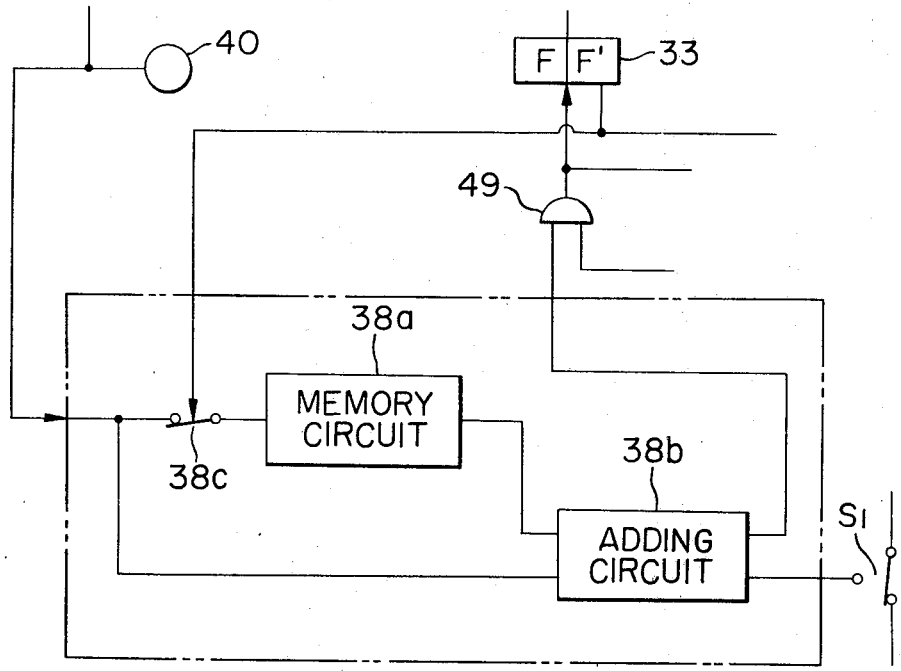
FIG. 5 is a diagram of a specific angle changing circuit for the polarizer.

In FIG. 5, reference character 38c is a memory switch adapted to assume an open (OFF) position upon reception of the output signal produced when the flip-flop circuit 33 has been set to its ON state. A memory circuit 38a serves to receive a signal corresponding to the amount of rotation of the polarizer 4 from a potentiometer 40 through the switch 38c and upon opening of the switch 38c, stores the output signal from the potentiometer 40 corresponding to the angle of rotation +45° or −45° of the polarizer, and delivers such signal to an adding circuit 38b which will hereinafter be described. The adding circuit 38b has two input terminals to which the signal from the memory circuit 38a (this signal being called signal A) and the signal from the potentiometer 40 (this signal being called signal B), and the adding circuit effects the calculation of A+B, the output signal of which is delivered to the servomotor 21 through the first change-over switch S1 and the servo amplifier 19. When A+B=0 (namely, if the memory circuit 38a, has stored therein the output signal from the potentiometer 40 corresponding to the angle of rotation +45° of polarizer 4, the polarizer has been rotated to its position of −45° so that the output signal from the potentiometer 40 corresponds to the angle of rotation −45° of the polarizer 4 is applied to the adding circuit 38b or, if the memory circuit 38a has stored therein the output signal from the potentiometer 40 corresponding to the angle of rotation −45° of the polarizer 4, the polarizer 4 is rotated to the position of + 45° so that the output signal from the potentiometer corresponding to the angle of rotation +45° of the polarizer 4 is applied to the adding circuit 38b), the signal from the adding circuit to the srvomotor 21 is zero and after all, this means that the polarizer 4 has been displaced from the position of +45° to the position of −45° or from the position of −45° to the position of +45°. When A+B ≠ 0, the adding circuit 38b delivers a low level signal to an AND circuit 49 which will hereinafter be described, and when A+B=0, the adding circuit 38b delivers a high level signal to the same AND circuit.

The memory switch 38c, the memory circuit 38a and the adding circuit 38b together constitute the first angle changing circuit.

Designated by 39 is a second angle changing circuit which controls the servo-motor 22 to displace the ½ wavelength plate 7 from the position of +$\theta_H$ to the position of −$\theta_H$ when the second change-over switch S2 has been changed over to connect the second angle changing circuit 39 to the servo amplifier 20 ( namely, when the projection 4a of the polarizer 4 strikes against the microswitch 27 or 28 when the position 7a of the ½ wavelength plate 7 strikes against the microswitch 30 or 31), the +$\theta_H$ representing the angle of rotation of the ½ wavelength plate 7 in such case.

Figure 6:
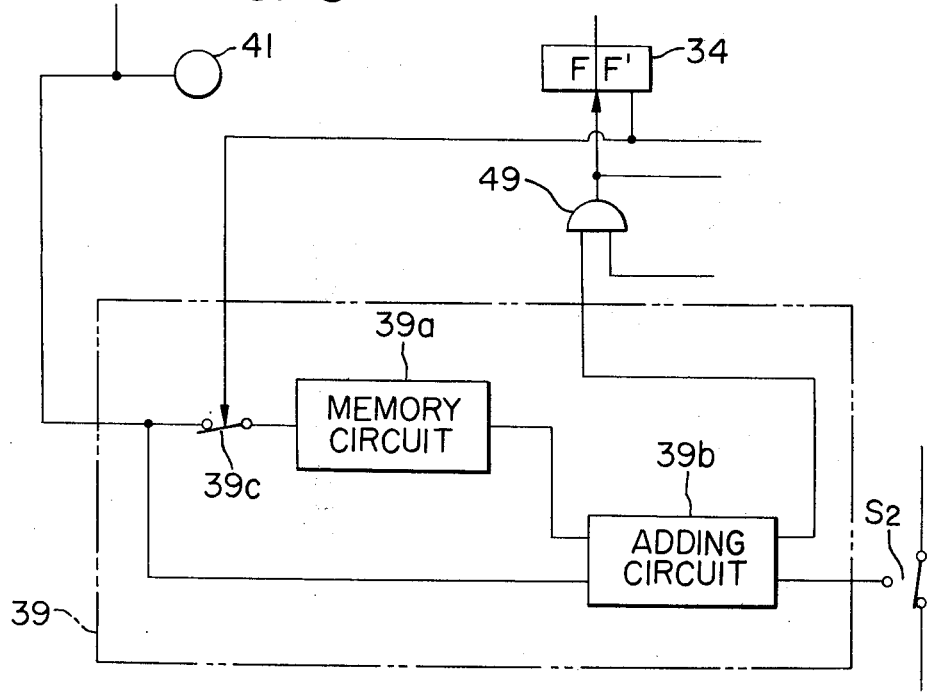
FIG. 6 is a diagram of a specific angle changing circuit for the ½ wavelength plate.

The second angle changing circuit will now be described by reference to FIG. 6. In FIG. 6, a memory switch 39c, a memory circuit 39a and an adding circuit 39b are similar to those which are described above and designated by 38a, 38c, and 38b, respectively. That is, the adding circuit 39b, upon displacement of the ½ wavelength plate 7 from the position of +$\theta_H$ to the position of −$\theta_H$, delivers a zero output signal to the servo-motor 20 and a high level signal to an AND circuit 49. The AND circuit 49 is a circuit which produces a high level output signal only when high level signals are applied to both of its two input terminals. The flip-flop circuit 33, which has so far been set to its ON state, is reset to its OFF state upon reception of the high level signal from the AND circuit 49.

Potentiometers 40 and 41 are provided to read the angles of rotation of the polarizer 4 and the ½ wavelength plate 7 and apply the signals resulting therefrom to operating circuits 42 and 44 which will hereinfter be described. The operating circuit 42 effects the calculation of 90°+2$\theta_P$, where $\theta_P$ is the angle of rotation of the polarizer 4, and delivers the result as output to an adding circuit 43. The operating circuit 44 effects the calculation of 2$\theta_H\theta$, where $\theta_H$ is the angle of rotation of the ½ wavelength plate 7, and delivers the result as output to an azimuth angle indicator circuit 45. A selecting circuit 46 is designed to deliver a 0° output signal to the adding circuit 43 when the output signal from the potentiometer 41 is positive and to deliver a +180° output signal to the adding circuit 43 when the output signal from the potentiometer 41 is negative. The adding circuit 43 effects the addition of the output signals from the operating circuit 42 and the selecting circuit 46, and delivers the result as output to a phase difference indicator circuit 47.

Operation of the first embodiment will now be described.

Generally, there is the following relation between the phase difference $\Delta$ and the amplitude-reflection ratio angle $\Psi$.

If the phase difference $\Delta$ is within the range of 0° ≦ $\Delta$ ≦ 180°, the amplitude-reflection ratio angle $\Psi$ assumes a positive value (that is, the output of the potentiometer 41 is positive). If the phase difference $\Delta$ is within the range of 180° ≦ $\Delta$ ≦ 360°, the amplitude-reflection ratio angle $\Psi$ assumes a negative value (that is, the output of the potentiometer 41 is negative).

When the projection 4a of the polarizer 4 is not in engagement with either of the microswitches 27 and 28 and the polarizing optical system is in extinguished condition, namely, when the light output signal from the analyser 11 is zero, it is defined that the azimuth angle of the polarizer 4 with respect to the reference azimuth is $\theta_P$ and that the azimuth angle of the ½ wavelength plate 7 with respect to the reference azimuth is 2$\theta_H$.

The azimuth angle $\theta_P$ of the polarizer 4 is read by the potentiometer 40 and the signal resulting therefrom is delivered from the potentiometer 40 to the operating circuit 42. The operating circuit 42 calculates 90°+2$\theta_P$ and delivers the output signal resulting therefrom to the adding circuit 43. When the polarizer 4 stops without the projection 4a striking against either of the microswitches 27 and 28, the phase difference $\Delta$ is within the range of 0° ≦ $\Delta$ ≦ 180°, and in such case, it follows from the aforesaid relation between the phase difference $\Delta$ and the amplitude-reflection ratio angle $\Psi$ that the output signal from the potentiometer 41 is positive. Therefore, the selecting circuit 46 delivers a 0° signal to the adding circuit 43, which in turn delivers a 90°+2$\theta_P$ signal to the phase difference indicator circuit 47, which thus indicates the value of 90°+2$\theta_P$.

On the other hand, the azimuth angle $\theta_H$ of the ½ wavelength plate 7 is read by the potentiometer 41 and delivered to the operating circuit 44. The operating circuit effects calculation of |2$\theta_H$|, and delivers the signal therefor to the azimuth angle indicator circuit 45, which indicates the value of |2$\theta_H$|.

Description will now be made of the operation in the case where the projection 4a strikes against either one of the microswitches 27 and 28, namely, where the phase difference $\Delta$ is within the range of 180° ≦ $\Delta$ ≦ 360°.

The case where the projection 4a strikes against the microswitch 27 will be taken as an example. When the projection 4a strikes against the microswitch 27, the switchh 27 is operated to set the flip-flop circuit 33 to its ON state, and by the output signal from the flip-flop circuit 33 in this state, the first change-over switch S1 is changed over from the preamplifier 17 side to the first angle changing circuit 38 side and the second change-over switch S2 is changed over from the preamplifier 18 side to the second angle changing circuit 39 side, so that the memory switch 38c in the first angle changing circuit 38 is opened, whereby the memory circuit 38a stores the output signal from the potentiometer 40 corresponding to the azimuth angle ±45° of the polarizer 4 and the second angle changing circuit 39 opens the memory switch 39c. Thus, the memory circuit 39a stores the output signal from the potentiometer 41 corresponding to the azimuth angle of the ½ wavelength plate 7 at that point of time (the point of time at which the memory switch 39c is opened), and also the flip-flop circuit 36 is set to its ON state and by the then output signal from the flip-flop circuit 36, the polarity changing circuit 37 is rendered operative to change the polarity of the alternating voltage $E_{x2}$ applied from the oscillator 23 to the K.D.P. light modulator element 8.

Thus, the change-over of the switch S1 results in the change-over from the connection to the conventional servo system 13, 14, 15, 17, S1, 19 and 21 for the polarizer 4 to the connection to the angle changing servo system 40, 38, S1, 19, 21, 33 and 49.

Also, the change-over of the switch S2 results in the change-over from the connection to the conventional servo system 13, 14, 16, 18, S2, 20 and 22 for the ½ wavelength plate 7 to the connection to the angle changing servo system 41, 39, S2, 20, 22, 34, and 49.

The angle changing servo system for the polarizer 4 controls the polarizer 4 until a signal corresponding to the azimuth angle −45° of the polarizer 4 is delivered from the potentiometer 40 to the adding circuit 38b, whereby the output from the adding circuit 38b to the servo-motor 21 becomes zero and the output to the AND circuit 49 assumes high level. Thus, when the control of the angle changing servo system for the polarizer 4 has completed, the polarizer 4 has changed its angle from the position of +45° to the position of −45°.

On the other hand, the angle chaning servo system for the ½ wavelength plate 7 controls the ½ wavelength plate 7 until a signal corresponding to the azimuth angle $-\theta_H$, opposite in sign to the azimuth angle $+\theta_H$, of the ½ wavelength plate at the point of time wherein the second change-over switch S2 is opened, is delivered from the potentiometer 41 to the adding circuit 39b so that the output from the adding circuit 39b to the servo-motor 20 becomes zero and the output to the AND circuit 49 assumes high level. Thus, when the servo control of the angle changing servo system for the ½ wavelength plate 7 has completed, the ½ wavelength plate 7 has changed its angle from the position of $+\theta_H$ to the position of $-\theta_H$.

With the high level signals thus applied to its two input terminals, the AND circuit 49 produces a high level signal at its output terminal, whereby the flip-flop circuits 33 and 34 so far set to their ON state are simultaneously reset to their OFF state by that high level signal. As the result, the first change-over switch S1 is changed over from the angle changing circuit 38 side to the preamplifier 17 side while the second change-over switch S2 is changed over from the angle changing circuit 39 side to the preamplifier 18 side, and the memory switches 38c and 39c are both closed. Thus, such change-over of the first change-over switch S1 has resulted in the change-over from the connection to the angle change-over servo system for the polarizer 4 back to the connection to the conventional servo system. Also, such change-over of the second change-over switch S2 has resulted in the change-over from the connection to the angle change-over servo system for the ½ wavelength plate 7 back to the connection to the conventional servo system.

Consequently, controls of the conventional servo systems for the polarizer 4 and the ½ wavelength plate, respectively, are effected until the polarizing optical system is rendered to its extinguished condition.

Let $\theta_P$ be the azimuth angle of the polarizer 4 with respect to the aforementioned reference azimuth when the polarizing optical system has been rendered to its extinguished condition, and $2\theta_H$ be the azimuth angle of the ½ wavelength plate 7 with respect to said reference azimuth.

The azimuth angle $\theta_P$ of the polarizer 4 is read by the potentiometer 40 and the signal resulting therefrom is delivered to the operating circuit 42, where the calculation of $90°+2\theta_P$ is effected. The output signal from the operating circuit 42 is delivered to the adding circuit 43. As will be seen from the relation between the aforementioned phase difference $\Delta$ and the amplitude-reflection ratio angle $\Psi$, the phase difference $\Delta$ is within the range of $180° \leq \Delta \leq 360°$ when the projection 4a strikes against either one of the microswitches 27 and 28, and therefore, the output signal from the potentiometer 41 is negative. Consequently, the selecting circuit 46 delivers a +180° signal to the adding circuit 43, which in turn delivers an output signal for $270°+2\theta_P$ to the indicator circuit 47, which thus indicates the value of $270°+2\theta_P$. On the other hand, the azimuth angle $-\theta_H$ of the ½ wavelength plate 7 is read by the potentiometer 41 and delivered to the operating circuit 44, where calculation of $|2\theta_H|$ is carried out. The output signal from the operating circuit 44 is delivered to the azimuth angle indicator circuit 45, which thus indicates the value of $|2\theta_H|$.

Figures 7, 7A:
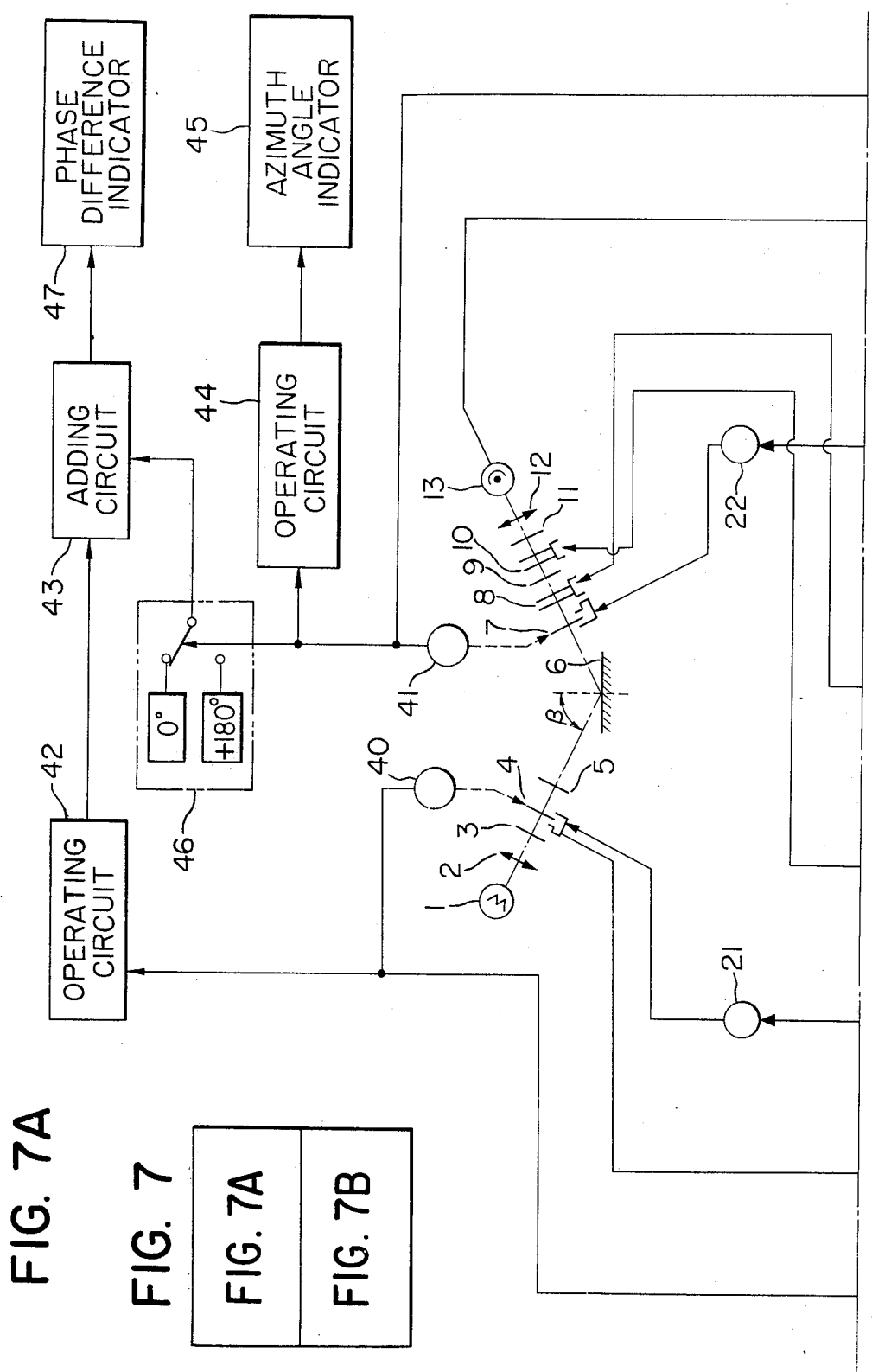
FIGS. 7, 7A and 7B show a second embodiment of the present invention.
Figure 7B:
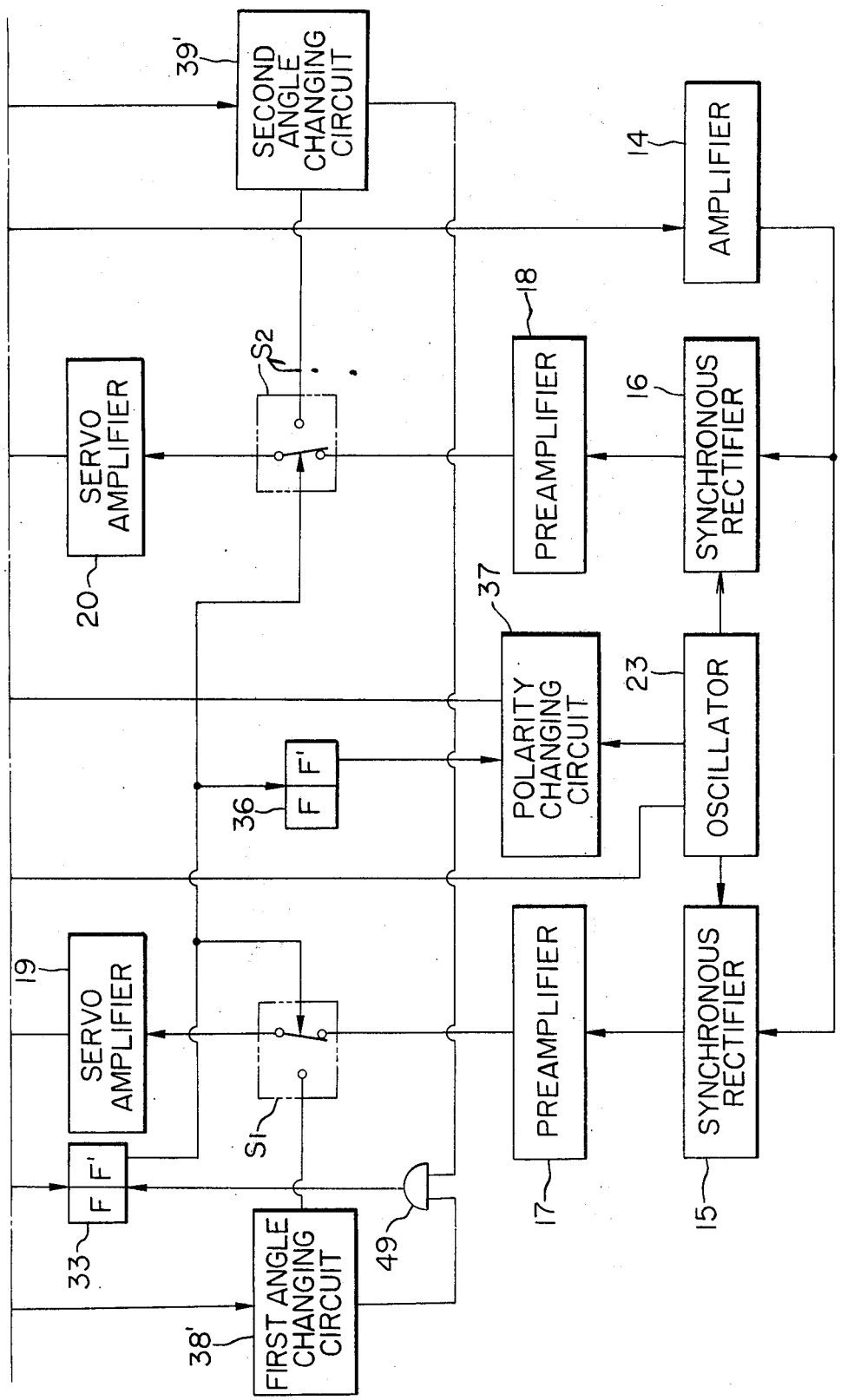

A second embodiment of the present invention is shown in FIG. 7. This embodiment is an automatic polarization analyser device in which the polarizer and the ½ wavelength plate are controlled so that engagementt of the projection 4a of the polarizer 4 with the microswitch 27 or 28 displaces the polarizer 4 from the position of +45° to the position of 0° or from the position of −45° to the position of 0° while displacing the ½ wavelength plate 7 from the position of $+\theta_H$ during the engagement to the position of 0°, whereafter the polarizing optical system becomes extinguished. The second embodiment is similar to the first embodiment with the exception that the flip-flop circuit 34 and the OR circuit 35 employed in the first embodiment are eliminated and that the first 38 and the second angle changing circuit 39 are replaced by similar angle changing circuits 38' and 39', respectively. The angle changing circuit 38' delivers the output of the potentiometer 40 to the servo amplifier 19 through the switch S1 and also delivers a low level signal to the AND circuit 49 when the output from the potentiometer 40 is other than zero, but a high level signal to the AND circuit 49 when the output from the potentiometer is zero. This circuit constitutes an angle changing servo system for the polarizer 4 for displacing the polarizer 4 from its position of +45° or −45° to its position of 0° when the projection 4a of the polarizer 4 is caused to strike against the microswitch 27 or 28 by the elements 40, 38', S1, 19, 21, 33 and 49 to shift the first change-over switch S1 from the preamplifier 17 side to the angle changing circuit 38' side.

The angle changing circuit 39' constitutes an angle changing servo system for the ½ wavelength plate 7 which delivers the output of the potentiometer 41 to the servo amplifier 20 through the switch S2 and also delivers a low level signal to the AND circuit 49 when the output potential from the potentiometer is other than zero, but a high level signal to the AND circuit 49 when the output potential from the potentiometer is zero.

Description will now be made of the operation of the second embodiment, particularly when the projection 4a of the polarizer 4 strikes against the microswitch 27 or 28, namely, when the phase difference $\Delta$ is within the range of $180° \leq \Delta \leq 360°$. When the projection 4a is out of engagement with the microswitch 27 or 28, the operation of the second embodiment is the same as that described with respect to the first embodiment. Engagement of the projection 4a with the switch 27 operates this switch to set the flip-flop circuit 33 to its ON state and in this state, the output signal from the flip-flop circuit 33 changes over the switches S1 and S2 to the changing circuit 38' side and the changing circuit 39' side, respectively, and also sets the flip-flop circuit 36 to its ON state. The change-over of the switch S1 renders operative the angle changing servo system for the polarizer 4, whereby the servo system controls the polarizer 4 until the output voltage from the potentiometer 40 to the changing circuit 38' becomes zero, namely, until the output signal from the changing circuit 38' to the switch S1 becomes zero and the output signal to the AND circuit 49 assumes high level.

On the other hand, the change-over of the switch S2 renders operative the angle changing servo system for the ½ wavelength plate 7, whereby this servo system controls the ½ wavelength plate until the output voltage from the potentiometer 41 to the changing circuit 39' becomes zero, namely, until the output signal from the changing circuit 39' to the switch S2 becomes zero and the output signal to the AND circuit 49 assumes high level. Thereafter, operation takes place just in the same manner as described with respect to the first embodiment.

I claim:

1. In an automatic polarization analyser device of the two modulation type having a polarizing optical system comprising a light source, a polarizer mounted for rotation about the optical axis of said system, a ¼ wavelength plate, a sample, a ½ wavelength plate mounted for rotation about said optical axis, an analyser, and photoelectric converter means arranged in the named order; a light modulator using two separable, distinct electrical signals to impart phase difference modulation and azimuth angle modulation to polarized light passed through said ½ wavelength plate; a first servo system responsive to a phase difference modulation signal in the output from said photoelectric converter means to control said polarizer until said modulation signal becomes zero; a second servo system responsive to an azimuth angle modulation signal in the output from said photoelectric converter means to control said ½ wavelength plate until said azimuth angle modulation signal becomes zero; a phase difference operating circuit for detecting the angle of rotation of said polarizer and effecting the operation of $90°+2\theta_P$ (where $\theta_P$ is the detected angle of rotation of said polarizer); and an azimuth angle operating circuit for detecting the angle of rotation of said ½ wavelength plate and effecting the operation of $|2\theta_H|$ (where $\theta_H$ is the detected angle of rotation of said ½ wavelength plate), the improvement comprising:

a third servo system for controlling said polarizer so as to change the azimuth angle thereof from +45° to −45° or from −45° to +45°;

a fourth servo system for controlling said ½ wavelength plate so as to change the azimuth angle thereof from $+\theta_H$ to $-\theta_H$ or from $-\theta_H$ to $+\theta_H$;

first detector means for detecting the angular displacement of said polarizer by +45° or −45° with respect to a reference position and for thereupon transferring from a reset condition, at which a reset sigal is produced to a set condition, at which a set signal is produced;

second detector means for detecting said angle changes by said third and fourth servo systems and thereupon producing a detection signal for transferring said first detector means to its reset condition;

first change-over means responsive to said first detector means for rendering said first and third servo system operative alternately such that upon reception of the set signal from said first detector means said first change-over means renders said first servo system inoperative but said third servo system operative and that upon reception of the reset signal from said first detector means said first change-over means renders said third servo system inoperative but said first servo system operative;

second change-over means responsive to said first detector means for rendering said second and fourth servo systems operative alternately such that upon reception of the set signal from said first detector means said second change-over means renders said second servo system inoperative but said fourth servo system operative and that upon reception of the reset signal from said first detector means said second change-over means renders said fourth servo system inoperative but said second servo system operative;

a circuit for changing the polarity of said electrical signal for said phase difference modulation upon reception of said set signal from said first detector means;

a selector circuit for producing a 0° signal when the angle of rotation of said ½ wavelength plate is of the positive sign and for producing a +180° signal when the angle of rotation of said ½ wavelength plate is of the negative sign; and a circuit for adding the output signals from said selector circuit and said phase difference operating circuit.

2. An automatic polarization analyser device according to claim 1, further comprising third detector means for detecting the angular displacement of said ½ wavelength plate by +45° or −45° with respect to the reference position and for thereupon transferring from a reset condition at which a reset signal is produced to a set condition at which a set signal is produced, and an OR circuit for receiving as one input the signals from said first detector means and as the other input the signals from said second detector means, said OR circuit producing a set signal, upon reception of a set signal at either one of said two inputs thereof, for causing said second change-over means to render said second servo system inoperative but said fourth servo system operative.

3. An automatic polarization analyser device according to claim 1, wherein said polarizing optical system is of the reflection type in which the ¼ wavelength plate has its azimuth angle set to −45° or +45° with respect to a reference azimuth (the surface of incidence of the sample) and said analyser has its azimuth angle set to 0° with respect to said reference azimuth when the azimuth angle of said ¼ wavelength plate is −45° and set to 90° when the azimuth angle of said ¼ wavelength plate is +45°.

4. An automatic polarization analyser device according to claim 1, wherein said polarizing optical system is of the transmission type in which said ¼ wavelength plate has its azimuth angle set to −45° or +45° with respect to a reference azimuth (the axial azimuth of said analyser) and said sample has its axial azimuth set in coincidence with said reference azimuth.

5. An automatic polarization analyser device according to claim 1, wherein said third servo system includes:

a first potentiometer for detecting the angle of rotation of said polarizer and producing an electrical signal corresponding thereto;

a first memory switch normally closed but opened by the set signal from said detector means;

a first memory circuit connected to said potentiometer through said memory switch to store the output signal from said potentiometer when said first memory switch is opened;

a first adding circuit receiving at one input thereof the output signal from said potentiometer and receiving at another input the output signal stored in said memory circuit, to effect the addition of the signals at said inputs and produce at one output a servo control signal corresponding to the result of the addition while producing at another output an angle change signal to be delivered to said second detector means; and a first servo-motor for receiving the servo control signal from said adding circuit to control said polarizer;

and wherein said fourth servo system includes:

a second potentiometer for detecting the angle of rotation of said ½ wavelength plate and producing an electrical signal corresponding thereto;

a second memory switch normally closed but opened by the set signal from said first detector means;

a second memory circuit connected to said second potentiometer through said second memory switch to store the output signal from said second potentiometer when said second memory switch is opened;

a second adding circuit receiving at one input thereof the output signal from said second potentiometer and receiving at another input the output signal stored in said second memory circuit to effect the addition of the signals at its said inputs and produce at one output a servo control signal corresponding to the result of the addition by the second adding circuit while producing at another output an angle change signal to be delivered to said second detector means; and a second servo-motor for receiving the servo control signal from said second adding circuit to control said ½ wavelength plate.

6. An automatic polarization analyser device according to claim 1, wherein said first detector means includes a flip-flop circuit.

7. An automatic polarization analyser device according to claim 1, wherein said second detector means comprises an AND circuit.

8. In an automatic polarization analyser device of the two modulation type having a polarizing optical system comprising a light source, a polarizer mounted for rotation about the optical axis of said system, a ¼ wavelength plate, a sample, a ½ wavelength plate mounted for rotation about said optical axis, an analyser, and photoelectric converter means arranged in the named order; a light modulator using two separable, distinct electrical signals to impart phase difference modulation and azimuth angle modulation to polarized light passed through said ½ wavelength plate; a first servo system responsive to a phase difference modulation signal in the output from said photoelectric converter means to control said polarizer until said modulation signal becomes zero; a second servo system responsive to an azimuth angle modulation signal in the output from said photoelectric converter means to control said ½ wavelength plate until said azimuth angle modulation signal becomes zero; a phase difference operating circuit for detecting the angle of rotation of said polarizer and effecting the operation of $90° + 2\theta_P$ (where $\theta_P$ is the detected angle of rotation of said polarizer); and an azimuth angle operating circuit for detecting the angle of rotation of said ½ wavelength plate and effecting the operation of $|2\theta_H|$ (where $\theta_H$ is the detected angle of rotation of said ½ wavelength plate), the improvement comprising:

a third servo system for controlling said polarizer so as to change the azimuth angle thereof from +45° to 0° or from −45° to 0°;

a fourth servo system for controlling said ½ wavelength plate so as to change the azimuth angle thereof from $+\theta_H$ to $-\theta_H$ or from $-\theta_H$ to $+\theta_H$;

first detector means for detecting the angular displacement of said polarizer by +45° or −45° with respect to a reference position and for thereupon transferring from a reset condition, at which a reset signal is produced, to a set condition, at which a set signal is produced;

second detector means for detecting said angle changes by said third and fourth servo systems and thereupon producing a detection signal for transferring said first detector means to its reset condition;

first change-over means responsive to said first detector means for rendering said first and third servo systems operative alternately such that upon reception of the set signal from said first detector means said first change-over means renders said first servo system inoperative but said third servo system operative and that upon reception of the reset signal from said first detector means said first change-over means renders said third servo system inoperative but said first servo system operative;

second change-over means responsive to said first detector means for rendering said second and fourth servo systems operative alternately such that upon reception of the set signal from said first detector means said second change-over means renders said second servo system inoperative but said fourth servo system operative and that upon reception of the reset signal from said first detector means said second change-over means renders said fourth servo system inoperative but said second servo system operative;

a circuit for changing the polarity of said electrical signal for said phase difference modulation upon reception of said set signal;

a selector circuit for producing a 0° signal when the angle of rotation of said ½ wavelength plate is of the positive sign and for producing a +180° signal when the angle of rotation of said ½ wavelength plate is of the negative sign; and a circuit for adding the output signals from said selector circuit and said phase difference operating circuit.

9. An automatic polarization analyser device according to claim 8, wherein said polarizing optical system is of the reflection type in which the ¼ wavelength plate has its azimuth angle set to −45° or +45° with respect to a reference azimuth (the surface of incidence of the sample) and said analyser has its azimuth angle set to 0° with respect to said reference azimuth when the azimuth angle of said ¼ wavelength plate is −45° and set to 90° when the azimuth angle of said ¼ wavelength plate is +45°.

10. An automatic polarization analyser device according to claim 8, wherein said polarizing optical system is of the transmission type in which said ¼ wavelength plate has its azimuth angle set to −45° or +45° with respect to a reference azimuth (the axial azimuth of said analyser) and said sample has its axial azimuth set in coincidence with said reference azimuth.

11. An automatic polarization analyser device according to claim 8, wherein said third servo system includes:

a first potentiometer for detecting the angle of rotation of said polarizer and producing an electrical signal corresponding thereto;

a first changing circuit for receiving the output signal from said first potentiometer and producing at one output thereof said output signal from said first potentiometer as a servo control signal and producing at another output an angle change signal to be delivered to said second detector means; and a first servo-motor for receiving the servo control signal from said first changing circuit to control said polarizer;

and wherein said fourth servo system includes:

a second potentiometer for detecting the angle of rotation of said ½ wavelength plate and producing an electrical signal corresponding thereto;

a second changing circuit for receiving the output signal from said second potentiometer and producing at one output thereof said output signal from said second potentiometer as a servo control signal and producing at another output an angle change signal to be delivered to said second detector means; and a second servo-motor for receiving the servo control signal from said second changing circuit to control said ½ wavelength plate.

12. An automatic polarization analyser device according to claim 8, wherein said first detector means includes a flip-flop circuit.

13. An automatic polarization analyser device according to claim 8, wherein said second detector means includes an AND circuit.

* * * * *